(12) United States Patent
Lavin et al.

(10) Patent No.: US 6,221,911 B1
(45) Date of Patent: Apr. 24, 2001

(54) USES FOR THYROID HORMONE COMPOUNDS OR THYROID HORMONE-LIKE COMPOUNDS

(75) Inventors: Thomas N. Lavin, Watchung, NJ (US); Anders B. Vahlquist, Uppsala (SE)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 08/973,627

(22) PCT Filed: Jun. 7, 1996

(86) PCT No.: PCT/US96/09975

§ 371 Date: Mar. 9, 1998

§ 102(e) Date: Mar. 9, 1998

(87) PCT Pub. No.: WO96/40048

PCT Pub. Date: Dec. 19, 1996

Related U.S. Application Data

(63) Continuation-in-part of application No. 08/481,698, filed on Jun. 7, 1995, now abandoned.

(51) Int. Cl.[7] .................................................. A61K 31/195
(52) U.S. Cl. ......................... 514/567; 514/859; 514/863
(58) Field of Search ..................................... 514/567, 859, 514/863

(56) References Cited

U.S. PATENT DOCUMENTS

| 5,118,707 | 6/1992 | Chatterjee et al. | 514/469 |
|---|---|---|---|
| 5,284,971 | * 2/1994 | Walker et al. | 562/429 |
| 5,869,470 | 2/1999 | Blank et al. | 514/159 |

OTHER PUBLICATIONS

CA 91:187087, Bukhonova et al., 1978.*

* cited by examiner

*Primary Examiner*—Kimberly Jordan
(74) *Attorney, Agent, or Firm*—Todd E. Garabedian; Wiggin & Dana

(57) ABSTRACT

This invention relates to the use of topically applied thyroid hormone compounds and thyroid hormone-like compounds which are receptor binding ligands, either agonists or antagonists, to improve the appearance of the skin and underlying subcutaneous fat and improve certain medical conditions when applied topically. These compounds can be used to treat skin conditions such as stria, cellulite, roughened skin, actinic skin damage, intrinsically aged skin, photodamaged kin, lichen planus, ichthyosis, acne, psoriasis, wrinkled skin, corticosteroid atrophy, collagen deficient skin, and to diminish the size and improve the appearance of skin scarring from surgical or naturally occurring wounds, and to reduce the incidence of hyperkeratotic scarring. The thyroid agonists and antagonists may also promote differentiation and amelioration of dedifferentiated skin in premalignant lesions. The thyroid agonists and antagonists can be active in all organisms which contain the thyroid hormone receptors, notably amphibians, birds and subjects. Combination with Vitamin D analogs, glucocorticoids, and retinoids will potentiate and modify the effects of the thyroid hormones for increased benefit. Side effects of thyroid hormones which occur when the hormone is given orally and prevent usefulness for the above conditions are prevented when the hormone is topically applied.

25 Claims, 10 Drawing Sheets

USES FOR THYROID HORMONE COMPOUNDS OR THYROID HORMONE-LIKE COMPOUNDS

This application is a 371 of PCT/US 96/09975, filed Jun. 7, 1996, which is a continuation in part of application Ser. No. 08/481,698, filed Jun. 7, 1995, now abandoned.

TECHNICAL FIELD

This invention relates to skin care preparations containing thyroid hormone compounds thyroid hormone metabolites, derivatives of those compounds and other thyroid hormone receptor binding chemical entities and to the use of such compositions including to correct skin abnormalities, to improve the appearance of the skin, and to control subcutaneous fat deposition when applied to the skin.

BACKGROUND

A wide variety of skin care preparations are currently available. There are currently available several preparations for the treatment of cellulite, a dimpling of the skin over excess superficial fat deposits, but these are believed to have doubtful efficacy. A wide variety of medically useful skin preparations are also currently available, comprising primarily glucocorticoids and retinoid topical medicaments, both of which have varying side-effects and usefulness. There is a considerable number of skin conditions and diseases such as stria, cellulite, roughened skin, actinic skin damage, intrinsically aged skin, photodamaged skin, lichen planus, ichtyosis, acne, psoriasis, wrinkled skin, eczema, seborrhoeic dermatitis, scleroderma, hyperkeratinizing disorders, keloids and skin scarring.

Eczema (dermatitis) is an itchy inflammation of the superficial skin layers caused by an outside agent or by endogenous factors. The terms dermatitis and eczema are used interchangeably.

The obvious treatment of eczema is to try to avoid precipitating factors.

Additionally, eczema is usually treated with topical steroids such as hydrocortisone, clobetasone butyrate, betamethasone and clobetasol propionate. The side effects of steroid use, particularly in the long term are well known and consist of skin atrophy, risk for systemic absorption of the drug and rebound phenomena when the drug is withdrawn.

There is a need for improved or alternate compositions for the treatment of dermatitis skin conditions such as psoriasis and eczema. New principles for treating eczema in particular should aim at reducing the reactivity of cutaneous cells, inhibiting cytokine release and improving the epidermal barrier recovery.

The structurally similar thyroid hormone compounds (3,3',5-triiodo-L-thyronine) triiodothyronine ($T_3$) and thyroxine L-thyroxine ($T_4$) have a very wide range of effects. In adult mammals they influence nearly all organs, the metabolism of nutrients, basal metabolic rate and oxygen consumption. In humans, the deficiency or excess of circulating thyroid hormone compounds results in the well characterised syndromes, hypo- and hyperthyroidism. Small concentrations of thyroid hormone metabolites which are also endocrinologically active exist. Among these thyroid hormone compounds are tri-iodothyroacetic acid("Triac" [4-(4-hydroxy-3-iodophenoxy)-3,5-diiodophenyl])acetic acid) and tri-iodoproprionic acid ("Tri-prop"[4-(4-hydroxy-3-iodophenoxy)-3,5-diiodophenyl]propionic acid).

Thyroid hormone compounds exert many of their actions by binding to a family of receptor proteins termed the C-erb-A family. In humans, this receptor protein family is now known to comprise several members, notably the human thyroid receptor alpha-1, the human thyroid receptor alpha-2 which binds the hormone poorly or not at all, the human thyroid receptor β-1, and the human thyroid receptor β-2. These proteins are part of a larger superfamily of steroid hormone receptors which comprises the glucocorticoid receptors, the retinoic acid receptors, the vitamin D receptors, and the insect moulting receptors—the receptors for ecdysone and the insect juvenile hormone compounds. Receptors for thyroid hormones are found in human skin, human fibroblasts and keratinocytes and they are also found in all other tissues within the human body (1).

In addition to the naturally occurring thyroid hormone compounds, a large number of chemical compounds which bind to the thyroid hormone receptor and which produce thyroid hormone-like effects have been synthesized see for example U.S. Pat. No. 5,401,772. For the purpose of this patent, the class of chemical entity which can act as a thyroid hormone compound but are not naturally occuring is defined herein as a 'thyroid-like compound'.

Thyroid hormone compounds, in many cases, act indirectly by influencing the effects of other hormones and tissues (1). For example in the rat, thyroid administration increases pituitary growth hormone production which in turn affects hepatic protein production including that of alpha-2 euglobulin. Functionally, in the rat, growth hormone may act as a second message for thyroid hormone(1). The biology of thyroid hormone compounds has been extensively studied after oral administration, which makes the relationship between a direct effect of thyroid hormone compounds and an indirect effect mediated by thyroid hormone modulation of other autocrine, paracrine or endocrine factors difficult to ascertain.

Orally administered thyroid hormone ($T_4$) influence the connective tissue biology of the skin. When given orally, thyroid hormone ($T_4$) induce an increase in neutral salt and acid soluble collagen, but decrease insoluble collagen in the skin of guinea pigs (2). Fibronectin production is decreased in human fibroblasts and fibroblast glycosoaminoglycans are either decreased or unchanged depending on the experimental conditions used (3,4,5,7,7a). Keratin gene expression for both the basal cell keratin K5 and K14 genes and the differentiation specific K10 gene is negatively regulated by thyroid hormones (9,8) in keratinocyte culture. These effects are mirrored by similar cell culture responses to retinoic acid (9) or the retinoid Tretinoin (19).

Histological studies of skin from individuals who have an excess of thyroid hormone compounds show an increased number of cell layers in the skin, reflected by mean epidermal cell number, increased protein turnover with increased proline incorporation and generalized increases in epidermal proliferation compared to normal skin (11). In individuals who have a lack of thyroid hormone compounds, the skin is atrophic with thinning of the epidermis and a decrease in cellularity. In human clinical biology, thyroid hormone excess leads to a general smoothing of the skin and the loss of wrinkles especially over the olecranon (elbow) surface.

Thyroid hormone compounds also accelerate fat synthesis and lipolysis (breakdown). In rats which have an excess of thyroid hormone compounds either chemically or by natural means, fat stores are in general decreased (12,13), although in humans clinical observation of thyroid hormone compound excess discloses either in increase of decrease in weight. The synthesis of fats may be increased (14,15) or decreased (12,13,16,21). Attempts to utilize the effects of excess oral thyroid hormone for weight loss in humans have in general failed because of severe adverse side effects (25,26).

Orally given thyroid hormone compounds in excess of normal bodily requirements or medical conditions which are associated with excess thyroid hormone compounds such as Grave's disease or toxic nodular goitre produce an acceleration of heart beat with associated heart failure, cardiac arrhythmias, osteoporosis, increased intestinal motility leading to diarrhoea, psychiatric abnormalities, and an increase in the basal metabolic rate. Attempts to use oral thyroid hormone compounds for diminishing lipid levels in man resulted in increased cardiac deaths (17).

RO76691 and 76692 respectively disclose an anti-wrinkle cream comprising a crude preparation from animal endocrine glands, including the thyroid gland, and a method of obtaining lipoid extracts from animal byproducts respectively. No data on the efficacy of the anti-wrinkle cream is provided nor is the thyroid hormone content of the cream provided or even mentioned. In particular, there is no suggestion in those patents of the efficacy of the compositions, methods, and uses of the present invention.

The use of Triac and its salts for a reduction of cellulite is disclosed in FR 2.153.202 (7134447). FR2197577 (72.30781) discloses various derivatives of Triac, including para hydroxy esters thereof, as having utility for the same indication. EP060776 discloses activity of an isopropyl derivative of Triac for the same indication. CH642851 (1168/80) discloses the utility of a liposome formulation of Triac together with glycosoaminoglycans for reducing cellulite. GB1354263 also discloses the use of Triac itself for reducing fat deposits. GB1400851 relates to the synthesis of ethyl esters and alkyl carboxy acids derivatives of Triac and their use in reducing cellulite in combination with leeches, hyaluronidase, proteases, and lipase.

None of the above publications disclose or suggest the usefulness of compounds selected from those that bind the thyroid hormone receptor. The relationship between Triac and thyroid hormones is not made in any of these patents and no data is presented to show the relationship of the above mentioned compounds to the thyroid hormone dependent endocrine system via an effect mediated through the human thyroid receptor. In fact, FR2354101 discloses the use of Triac as an inhibitor of phosphodiesterase and its effect to increase cyclic AMP. This effect occurs only at dose ranges of approximately $10^{-4}$ M in in vitro experiments using isolated adipocytes. In concert with this mode of activity, the prior art literature makes claims for effective concentrations of chemical entity for anti-cellulite effects as greater than 50 mg of Triac or Triac derivative per 100 ml of vehicle and usually between 100 and 200 mg/100 gms of excipient.

FR96.171 discloses the topical cellular growth accelerating activity and mitogenic of thyroxine (0.001–0.008 mg. %) in a propylene glycol diethyl ether vehicle in rat skin. No mention is made of other compounds which have thyroid hormone receptor binding activity such as Triac or Triiodothyronine, or other thyromimetic compounds known at the time (Journal of Medicinal Chemistry, 6, p 554–563, 1963). No teaching concerning the effects of thyroid hormone receptor binding entities on epidermal differentiation, gene expression or keratinization is made. GB782,745 and 859,546 describe the topical usefulness of compounds of a class which partially overlap with chemical entities which bind to the thyroid hormone receptor, but includes compounds including L-T-1 with no thyroid hormone receptor binding activity, and only a small subset of compounds which do recognize the receptor. In these patents, no claims are made for chemical entities characterized by binding to the thyroid hormone receptor or having thyroid hormone like activity. U.S. Pat. No. 3,198,702 discloses a method of treating burns comprising the topical application of certain thyroxin analogues which are a subset of the same class of compounds claimed to have activity in GB 782745 and 859546.

No prior art document discloses the skin differentiating and collagen promoting effects of thyroid hormone or its analogues.

SUMMARY OF THE INVENTION

According to one aspect of the invention there is provided a composition for topical application, the composition comprising at least one thyroid hormone compound or thyroid hormone-like compound together with a pharmacologically acceptable base.

The topically-applied thyroid hormone compounds, or thyroid hormone-like compounds used in the compositions and methods of the present invention are advantageous in that they enable the use of these chemical compounds to control subcutaneous or dermal fat stores to improve the appearance of the skin, or normalize the physiology of the skin under pathophysiologic conditions without causing the undue adverse effects of orally administered thyroid hormone compounds in a direct thyroid hormone dependent manner avoiding renal and hepatic metabolism of the thyroid hormone receptor binding chemical entity. In particular, the method of delivery of the thyroid hormone compounds and thyroid hormone-like compounds avoids liver and kidney metabolism of the hormones, blood circulation of the hormones to other tissues and binding to blood carrier proteins which can alter efficacy.

For the purposes of this invention a "thyroid hormone compound" or "thyroid hormone-like compound", which terms are used interchangeably herein, is any chemical entity, including peptides, which binds to thyroid hormone receptor TR-α or β with a dissociation constant, $K_d$, lower than 1 μM when tested in receptor binding assay, described by Lavin (27) using pure or substantially pure natural or recombinant thyroid hormone α or β receptor containing the ligand binding domain or thyroid hormone receptor containing preparations such as rat nuclei. Such ligands may be considered agonists when they have similar agonistic effects as the natural hormone or may be considered antagonists when the compounds antagonize the effects of the natural hormone compounds. Partial agonist/antagonists also may exist. (Suitable ligands may be agonists or antagonists).

The topically-applied thyroid hormone compounds, or thyroid hormone-like compounds used in the compositions and methods of the present invention are advantageous in that they enable the use of these chemical compounds to control subcutaneous or dermal fat stores, to improve the appearance of the skin, or normalize the physiology of the skin under pathophysiologic conditions without causing the undue adverse effects of orally administered thyroid hormone compounds. In particular, the method of delivery of the thyroid hormone compounds and thyroid hormone-like compounds avoids liver and kidney metabolism of the hormones, blood circulation of the hormones to other tissues and binding to blood carrier proteins which can alter efficacy.

The thyroid hormone compound or thyroid hormone-like compound is preferably in pure form, i.e. not contaminated with other similar compounds.

The said at least one thyroid hormone compound or thyroid hormone-like compound may be selected from, for example, one of the following illustrative list of compounds:

Tri-iodothyronine (3,5,3'-triiodothyronine, T3); D and L thyroxine (T4); 3,3'5'tri-iodothyronine (reverse T3); 3,3'-diiodothyronine; T3 and T4 analogues such as 3,5,3',-Triiodo-L-thyronine methyl ester; 3,5,3'-Triodo-L-thyronine hydrochloride; L-thyroxine hydrochloride; Tetrac (3-[4-(4-hydroxy-3,5-diiodophenoxy)-3,5-diiodophenyl]acetic acid); Triac ([4-(4-hydroxy-3-iodophenoxy)-3,5-diiodophenyl] acetic acid); Tetraprop; Triprop ([4-(4-hydroxy-3-iodophenoxy)-3,5-diiodophenyl]propionic acid); T4Bu; T3Bu; Thyroxamine; Triiodothyronamine; (5-Benzyloxy-2-methoxyphenyl)-(2-methoxypyrimidin-5-yl)-methanol; Benzyloxy-2-methoxyphenyl)-(6-methylpyridin-3-yl) methanol; (5-Benzyloxy-2-methoxyphenyl)-(5-bromo-2-methoxypyridin-4-yl)methanol; (5-benzyloxy-2-methoxyphenyl)-(2,6-difluoropyridin-3-yl)methanol; (5-Benzyloxy-2-methoxyphenyl)-(2-methoxypyridin-4-yl) methanol; 4-Methoxy-3-[(2-methoxypyrimidin-5-yl) methyl]phenol; 4-Methoxy-3-[6-methylpyrid-3-yl)methyl] phenol; 5-Benzyloxy-2-methoxybenzyl Bromide; (5-Benzyloxy-2-methoxyphenyl-(6-chloropyridazin-3-yl)-acetonitrile; 4-Benzyloxy-2-[2-methoxythiazol-5-yl) methyl]anisole; 6-[(5-Hydroxy-2-methoxyphenyl)methyl] thiazol-2-(3H); 3'-Heteroarylmethyl-4'-)-methyl-3,5-dinitro-N-trifluoro-acetyl-L-thyronine ethyl esters; 3'-heteroarylmethyl-3,5-di-iodo-4')-methyl-N-trifluoro-acetyl-L-thyronine Ethyl Esters; 3'-heteroarylmethyl analogues of 3,3',5-tri-iodo-L-thyronine (T3); 3'-substituted derivatives of the thyroid hormone 3,3'5-triiodo-L-thyronine (T3); L-3,3'-T2; DL-Br2I; L-Br2IPr; L-Me2I; L-Me3; L-Me4; L-Me2IPr; DL-IMeI; L-3,5-Dimethyl-3'-isopropylthyronine (DIMIT); DL-BPT4; B-triac; BP-tetrac; DL-SBT3; DL-SBT4; DL-MBT3; MB-tetrac; T2F; T2Cl; T2Br; T2Me; T2Et; T2iPr; T2nPr; T2sBu; T2tBu; T2iBu; T2Phe; T2F2; T2Cl2; T2Me2; 3,5,3'-Triiodo-D-thyronine; 3,5-Diiodo-4-hydroxyphenylpropionic acid (DIHPA); Aryloxamic acids; (arylamino)acetic acids; arylpropionic acids; arylthioacetic acids; (aryloxy)acetic acid; 3,3'-T2; 3,5-T2; 3',5'-T2; α-methyl-3,5,3'-triiodothyroacetic acid, α-methyl-3,5,3'-triiodothyropropionic acid, and α-methyl-3,5,3',5'-tetraiodothyropropionic acid; methylene- and carbonyl-bridged analogs of iodinated thyronines or thyroacetic acids or iodinated benzofurans; 3,5-diiodo-4-(2-N,N-diethylaminoethoxy)phenyl-(2-butylbenzofur-3-yl) methanol hydrochloride; 2-methyl-3-(3,5-diiodo-4-(2-N,N-diethylamino-ethoxy)-benzoyl)benzofuran hydrochloride; 2-n-butyl-3-(3,5-diiodo-4-carboxymethoxy-benzoyl) benzofuran; 2-methyl-3-(3,5-diiodo-4-hydroxy-benzoyl) benzofuran; 2-methyl-3-(3,5-diiodo-4-carboymethoxy-benzyl)benzofuran; [4'-hydroxy-3'-iodo-3,5 diiodo-4-(2-N, N-dimethylamino-ethoxy)benzophenone hydrochloride; 2-butyl-3-(3-iodo-4-hydroxybenzoyl)benzfuran; 4",4-dihydroxy 3'3,5-triiodo-diphenylmethane; 3,5-diiodo-4-(2-N,N-diethylaminoethoxy)phenyl-(2-butylbenzofur-3-yl) methanol hydrochloride; 2-methyl-3-(3,5-diiodo-4-(2-N,N-diethylamino-ethoxy)-benzoyl)benzofuran hydrochloride; 2-n-butyl-3-(3,5-diiodo-4-carboxymethoxy-benzoyl) benzofuran; 2-methyl-3-(3,5-diiodo-4-hydroxy-benzoyl) benzofuran; 2-methyl-3-(3,5-diiodo-4-carboxymethoxy-benzyl)benzofuran; 4'-hydroxy-3'-iodo-3,5-diiodo-4-(2-N, N-dimethylamino-ethoxy)benzophenone hydrochloride; 2-butyl-3-(3-iodo-4-hydroxybenzoyl)benzofuran; 4',4-dihydroxy-3'3,5-triiodo-diphenylmethane; 3,5-diethyl,3'-isopropyl thyronine (DIET); and IpTA2 (3,5 diiodo-3'isopropyl thyroacetic acid) and pharmacologically acceptable salts and derivatives thereof.

Other suitable thyroid hormone-like compounds, are disclosed for example in U.S. Pat. Nos. 5,284,971, 5,401,772, 3,649,679, 3,357,887, 412,579, 4,168,385, 5,179,097, EP0580550, EP018351 and H. A. Selenkow and S. P. Asper. Jr., Physiol. Rev. 35 426 (1955); C. S. Pitman and J. A. Pitman In Handbook of Physiology, Section 7: Endocrinology, Vol. 3, R. O. Greep and E. B. Astwood. Eds., Thyroid American Physiological Society, Washington D.C., 1974, p. 233; E. C. Jorgensen, Pharm. Ther. B, 2, 661 (1976); and E. C. Jorgensen, "Thyroid Hormones and Analogs. II. Structure-Activity Relationships," in Hormonal Proteins and Peptides, Vol. 6. Thyroid Hormones, C. H. Li, Ed., Academic, New York, 1978, p. 108. The choice of other suitable thyroid hormone-like compounds for use in the compositions and methods of the present invention is within the scope of the skilled worker.

Preferably, the composition is in the form of a cream although other forms of preparation which can be readily applied to the skin, such as lotions, topical sprays, liposomes, solutions or emulsions, are contemplated. Preferably the composition includes suitable epidermal penetration enhancing agents.

Preferably, the composition comprises less than about 50 mg/100 ml, more preferably less than about 10 mg/100 ml of the said at least one thyroid hormone compound or thyroid hormone-like compound. Preferably the composition comprises a concentration $5 \times 10^8$ times or less the receptor dissociation constant, $K_d$ of the said at least one thyroid hormone compound or thyroid hormone-like compound. Preferably the composition is used to supply an effective amount of the thyroid hormone compound or thyroid hormone-like compound which generally ranges from 500 mg/m$^2$ to 0.1 mg/m$^2$ in one or more applications, preferably 250 mg/m$^2$ to 1 mg/m$^2$ per day in one or more applications.

The effective concentration will depend on factors such as metabolism of the compound and its effective octanol/water partition coefficient and which can be readily determined by the skilled addressee. The composition of the invention may also include other ingredients such as Vitamin D, glucocorticoids and retinoids or analogues thereof to potentiate and modify the effects of the thyroid hormone compound or thyroid hormone-like compound for increased benefit. In particular when the composition is formulated for lipolytic activity it may contain derivatives of medicinal herbs such as Guto Kola, (*Centella asiatica*), *Cola nitada*, Khella (*Amni visnaga*), cola nut, *Camellia Suiensis*, Guavana, clove, coffee. The composition may also include BHT (butylated hydroxy toluene) or BHA (butylated hydroxy anisole) as a hindered phenol to decrease iodine decomposition or substances. Furthermore, the composition may include compounds which facilitate passage of the thyroid hormone through the skin and compounds which act as sunscreens such as PABA Preferably, the composition also includes a suitable antioxidant such as Tinuvin P or BHA. The choice of such compounds is within the scope of the skilled addressee. See for example Hermens W. A. J. J Pharmaceutisch Weekblad Scientific Edition 14(4A) 1992.

Preferably, the thyroid hormone compound or thyroid hormone-like compound is not halogenated as such compounds are less prone to photodecomposition. The pharmacologically acceptable base is preferably an oil in water emulsion or an alcoholic solution with glycerol.

The said at least one thyroid hormone compound or thyroid hormone-like compound is preferably at least partially dissolved in a solvent. The solvent is preferably an organic solvent selected from alcohol and alcohol and water solutions. More preferably, the organic solvent is selected from isopropanol, isopropanol and water, ethanol, and ethanol and water solutions containing at least 20% alcohol.

According to a further aspect of the invention there is provided a unit dose package containing a single dose of a composition in accordance with the first aspect of the invention.

According to a further aspect of the invention there is provided a method of improving the condition or appearance of the skin of a subject, the method comprising the steps of:

providing a composition in accordance with the first aspect of the invention; and applying the said composition to the skin of the subject.

The method improves conditions selected from for example, stria, cellulite, roughened skin, actinic skin damage, intrinsically aged skin, photodamaged skin, lichen planus, ichthyosis, acne, psoriasis, wrinkled skin (whether deep or superficial), Dernier's disease, eczema, atopic dematitis, seborrhoeic dermatitis scleroderma, collagen deficient skin, corticosteroid atrophy, chloracne, pityriasis, hyperkeratinizing disorders, keloids and skin scarring.

Preferably, the composition is applied from twice a day to every three days.

According to a further aspect of the invention there is provided a method of reducing cutaneous or subcutaneous fat deposits in a subject, the method comprising the steps of:

providing a composition in accordance with the first aspect of the invention; and applying the said composition to skin of the subject in the vicinity of the deposits to be treated.

In a preferred embodiment, the fat deposits cause cellulite.

Preferably, the composition is applied to the skin from between twice a day to every three days.

Preferably, the subject is a mammal, more preferably a human. The thyroid hormone compound and thyroid hormone-like compound can be active in all organisms which contain thyroid hormone receptors, notably amphibians, birds and mammals.

According to another aspect of the invention there is provided the use of a thyroid hormone compound or thyroid like compound in the preparation of a composition for topical application to the skin of a subject in order to improve the condition of that skin or reduce cutaneous or subcutaneous fat deposits.

DETAILED DESCRIPTION OF THE INVENTION

Compositions in accordance with the invention and methods for their use will now be described, by way of example only, of with reference to the accompanying drawings, FIGS. 1–8.

EXAMPLE 1

IN VITRO TESTS WITH A SKIN A MODEL

Figure 1:
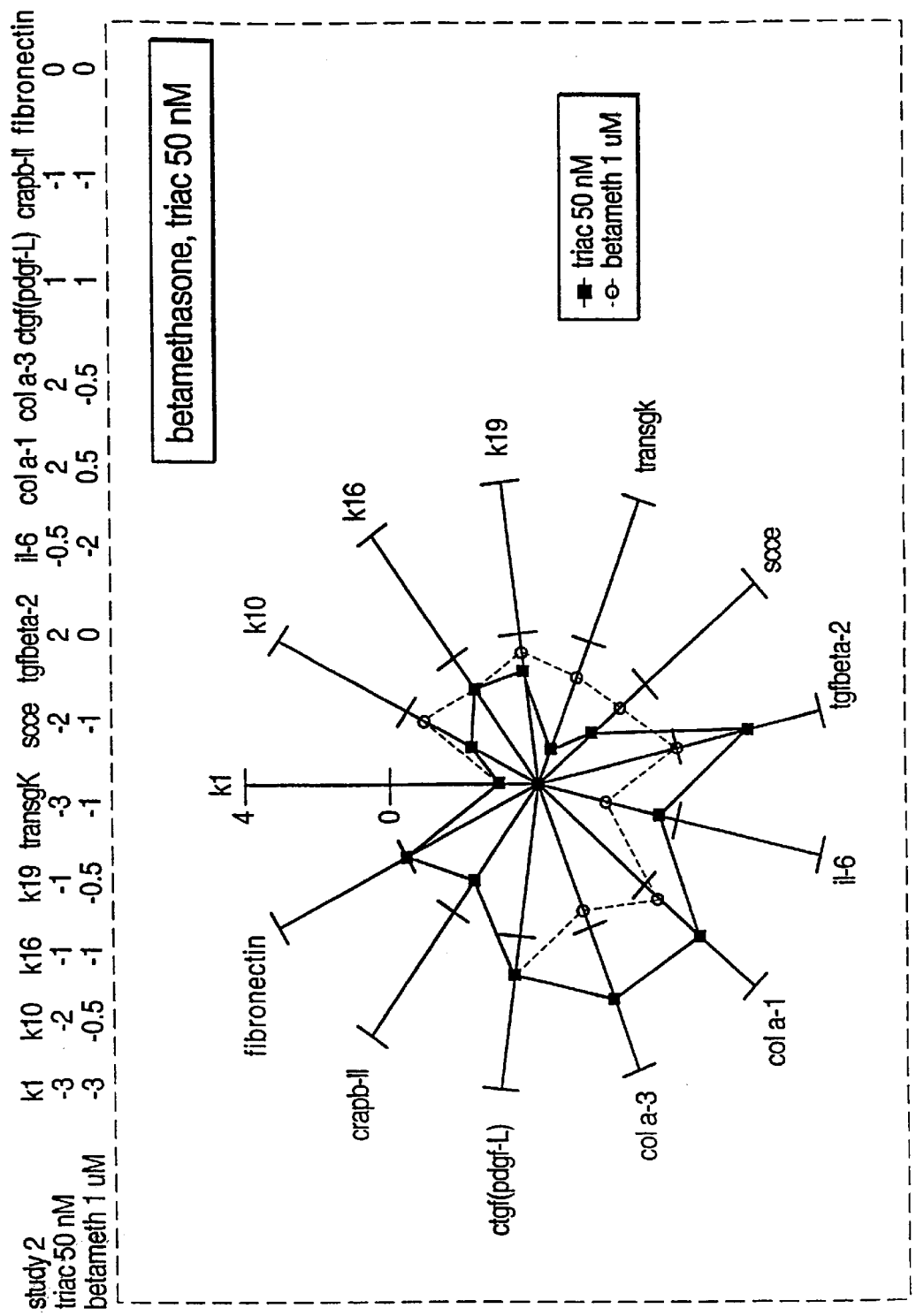
FIG. 1 is a graph showing the comparative effect of betamethasone and Triac on the Skin-2 model.

Regulation of epidermal genes which regulate collagen production and promote epidermal differentiation.

Terminal differentiation of the epidermal layer of the skin is thought to be related at least in part to the activity of tranglutaminase K and the production of cornified envelopes (Febs Letter 258 p35–38, 1989, and J. Invest. Derm. 90 p472). It is thought that the ability of a retimoid to down regulate transglutaminase K in cultured cells is an indication of its ability to effectively treat psoriasis (EP00465343). TGF beta 1 and 2 are thought to promote terminal differentiation and inhibit basal cell proliferaton (Fuchs E. J. Cell Biol. 111 p2807). A protease, stratum corneum chymotryptic enzyme, SCCE, is produced by keratinocytes and is thought to promote shedding of skin cells in the upper granular layer of the epidermis and be related to epidermal differentiation (Egulrud et al, ACTA DERM Venereol. Vol 73 p 181–184 1993: Sondell etal, J. Invest Derm 1995, p 819–823). Further, in hyperproliferating skin, the keratins 1 and 10 (differentiation markers) are reduced and the hyperproliferation keratins 16 and 6 are increased (West et al 1992, J. Invest. Derm. 1 p 95). Retinoic acid effects on skin keratinocytes in culture reflect a decrease in the differentiation markers and variable changes in keratins 6 and 16 and they also decrease transglutaminase K in vitro. Both these markers, the keratins and tranglutaminase K have been considered in-vitro measures of retinoic acid analogs dermatologic potency and usefullness (Kopan and Fuchs, J. Cell Biol 105 p 427–440, 1987 and Griffiths et al, Br J Derm 1992, 127 suppl 4 p 21. Paradoxically, however, retinoids are active against hyperproliferating disorders and increase the keratin 1 and 10 differentiation markers and tranglutaminase K in vivo after topical application. (Griffiths et al, Br. J. Derm 1992, 127 suppl 4 p21. In keratinocyte cultures, thyroid hormone compounds decreases keratin genes K5, K14 and K10 (6,10). modulation of the keratin 1 gene by thyroid hormone compounds has not been previously reported.

Collagen production in the skin occurs from a variety of collagen genes, with the procollagen A-1 and A-3 genes most studied. Collagen is decreased in glucocorticoid treated skin (7) and in photodamaged skin (24). It is thought that overproduction of collagen in the hyperproliferative state may contribute to keloidal scar production. Furthermore, CTGF, a PDGF like peptide (PDGF-L) that is produced in response to TGF beta-1 appears to be present in increased amounts in fibrosing disorders such as schleroderma. In cultured human fibroblasts, thyroid hormone administration decreases collagen production (de Rycker et al, FEBS Lett, vol 174 p34–37 1984).

No universally accepted model of human skin exists. A novel synthetic human skin, Skin-2 model ZK1301

(Advanced Tissue Sciences, La Jolla (USA)) is composed of a three dimensional human skin culture consisting of a dermal fibroblast layer and human foreskin keratinocytes which can be grown with an air-keratinocyte interface to promote normal differentiation and cornification of the model skin. The Skin-2 model is widely accepted as an in-vitro model to asess cutaneous toxicity (Rheins et al, Toxic, in Vitro, 8, no. 5 p1007–1014 1994 and is approved by the Canadian and U.S. FDA as an appropriate model for testing skin toxicity. Such a model has the following advantages:

1) The keratinocytes differentiate in a manner very similar to the in vivo state. A stratified multilayered epithelium with all the markers and properties of such epithelium forms. This never happens in typical keratinocyte culture.

2) The presence of fibroblasts allows the detection of fibroblast markers including collagen. The interplay between keratinocytes and fibroblasts which occurs in vivo also is mimicked in the SKIN$^2$ model, which allows paracrine functioning of the cell types. We assessed the ability of multiple thyroid hormone receptor binding ligands, and several therapeutically useful model compounds including retinoic acid to alter mRNA production of a variety of genes present in fibroblasts and keratinocytes present in the Skin-2 model.

Materials and Methods

The following were components of the Skin$^2$ kits: 9×9 mm skin tissues on agarose, 6-well plates, and Millicell inserts. Two media based on Dulbecco's Modification of Eagle's medium were also included:

Maintenance medium (containing 5% fetal calf serum) and serum-free assay medium.

The following were supplied by other sources: "Stripped" (Samuels, H. et al, Endocrinology 105, p80–85, 1979) fetal calf serum and all substances to be tested were from Karo Bio AB. All-trans-retinoic acid, 1,25-(OH)2-vitamin D3, and betamethasone were purchased from Sigma Chemicals (Stockholm). Upon arrival the skin tissues were placed dermal-side down into the center of a Millicell in a 6-well plate well containing prewarmed maintenance medium. The tissues were incubated at 37° C. in an atmosphere of 5% $CO_2$ in air. After 24 h the maintenance medium was exchanged.

Following another 24 h the Maintenance medium was removed and replaced by Serum-free assay medium containing 5% "stripped" fetal calf serum. Substances were added within 1 h after medium exchange and the tissues were incubated for 10 or 48 h in the presence of the substances. Medium and substances were changed after 24 h incubation. The cells were grown at an air—liquid interface. At the end of the 48 h-incubation period two tissues were pooled together in a sterile plastic centrifugation tube. The tissue was snap frozen on solid ice (−60° C.) and stored at −70° C. until used. Duplicate samples were included for each treatment.

Analysis of mRNA Expression in Skin$^2$ by Reversed-Transcriptase Coupled to Polymerase Chain Reaction (RT-PCR)

Total RNA was extracted from Skin$^2$-samples and human skin biopsies using Ultraspec II (Biotecx Laboratories, Inc., Houston, Tex.). One ml of Ultraspec II was added to each sample which were homogenized by using a Polytron for 2×20 sec at setting 6. Total RNA was extracted according to the protocol supplied by the manufacturer. The amount of RNA was quantitated by measuring the absorbance at 260 nm. The A260/A280-ratio of the extracted RNA was generally between 1.75 and 2.0. Three µg RNA was reversed transcribed into cDNA in a 30 ul mixture containing 50 mM Tris-HC (pH 8.3), 75 mM KC, 3 mM MgC2, 10 mM dithiothreitol, 0.5 mM of each dNTP, 200 U M-MLV reversed transcriptase (Life Technologies), 25 U placental Rnase inhibitor (Boehringer-Mannheim) and oligo d(T)15 as primer. After incubation at 37° C. for 60 min, the reaction was stopped by heating at 75° C. for 10 min and the mixture stored at −70° C. until cDNA amplification was performed.

Polymerase Chain Reation

The following PCR mixture (24 µl) was prepared immediately before use: 10 mM Tris-HC (pH 8.3), 50 mM KC, 1.5 mM MgCl, 200 µM of each dNTP, 0.5 µM primers (see Table 1), and 0.5 U Taq DNA polymerase licensed for PCR (Life Technologies). The tubes were placed in a Thermal cycler (Perkin-Elmer) programmed as follows: (a) 90° C. for 90 s; (b) variable number of cycles (see Table 1) of the following sequential steps: 60 s at 94° C., 75 s at annealing temp (see Table 1), 90 s at 72° C.; and (c) 7 min at 72° C.

After mixing 7.5 µl of PCR-products with 2 µl of loading buffer, samples were separated by electrophoresis on a 1.2% agarose gel containing ethidium bromide, and visualized by UV transillumination. Gels were recorded by videoprints.

The amount of product was estimated on the videopoint or directly on the gel. The amount of transcripts in each lane were compared in relation to two control samples run in parallel.

The expression of certain genes was not modulated by test compounds, and so these genes were not selected as markers in subsequent experiments

TABLE 1

| Gene | Annealing Temp | PCR-cycles | Product Size (bp) |
| --- | --- | --- | --- |
| Fibronectin | 60° C. | 22–25 | 794.0000000 |
| IL-6 | 60 ° C. | 22–25 | 639.0000000 |
| IL-8 | 60° C. | 25.0000000 | 275.0000000 |
| ICAM-1 | 60° C. | 30.0000000 | 727.0000000 |
| TGF β1 | 60° C. | 25.0000000 | 338.0000000 |
| TGF β2 | 56° C. | 40.0000000 | 575.0000000 |
| Keratin 1 | 60° C. | 24–27 | 480.0000000 |
| Keratin 10 | 60° C. | 27–30 | 439.0000000 |
| Keratin 5 | 60° C. | 25.0000000 | 559.0000000 |
| Keratin 14 | 60° C. | 25.0000000 | 651.0000000 |
| Keratin 6 | 60° C. | 25.0000000 | 464.0000000 |
| Keratin 19 | 60° C. | 20.0000000 | 400.0000000 |
| Keratin 16 | 60° C. | 22–25 | 725.0000000 |
| SCCE | 60° C. | 22.0000000 | 463.0000000 |
| Collagenase | 60° C. | 30.0000000 | 463.0000000 |
| Involucrin | 60° C. | 25.0000000 | 541.0000000 |
| Filaggrin | 60° C. | 29.0000000 | 526.0000000 |
| Loricrin | 60° C. | 33.0000000 | 663.0000000 |
| Procollagen 1A1 | 60° C. | 20–22 | 620.0000000 |
| Procollagen 1A2 | 60° C. | 23.0000000 | 712.0000000 |
| Procollagen 3A1 | 60° C. | 20–24 | 524.0000000 |
| TGk | 60° C. | 22–30 | 652.0000000 |
| CTGF | 60° C. | 25.0000000 | 515.0000000 |
| ThR θ | 60° C. | 32.0000000 | 623.0000000 |
| ThR β | 60° C. | 32.0000000 | 578.0000000 |
| CRBPI | 60° C. | 25.0000000 | 388.0000000 |
| CRABPII | 60° C. | 22–25 | 402.0000000 |
| RAR θ | 60° C. | 35.0000000 | 817.0000000 |
| RAR β | 60° C. | 35.0000000 | 769.0000000 |
| RAR | 60° C. | 30.0000000 | 765.0000000 |
| RXR θ | 60° C. | 30.0000000 | 743.0000000 |
| VDR | 60° C. | 30.0000000 | 888.0000000 |
| cyclophilin | 60° C. | 20–22 | 424.0000000 |
| GAPDH | 60° C. | 24–27 | 893.0000000 |

Key

IL-6 interleukin-6, IL-8 interleukin-8, ICAM-1 intracellular adhesion molecule-1, TGF β transforming growth factor, SCCE stratum corneum chymotryptic enzyme, $TG_k$ keratinocyte transglutaminase, CTGF connective tissue growth factor, ThR thyroid hormone receptor, CRBP cellular retinol-binding protein CRABP II cellular retinoic acid-binding protein, RAR retinoic acid receptor, RXR retinoid X receptor (9-cis-RA receptor), VDR vitamin $D_3$ receptor, GAPDH glyceraldehyde-3-phosphate dehydrogenase.

Figure 2:
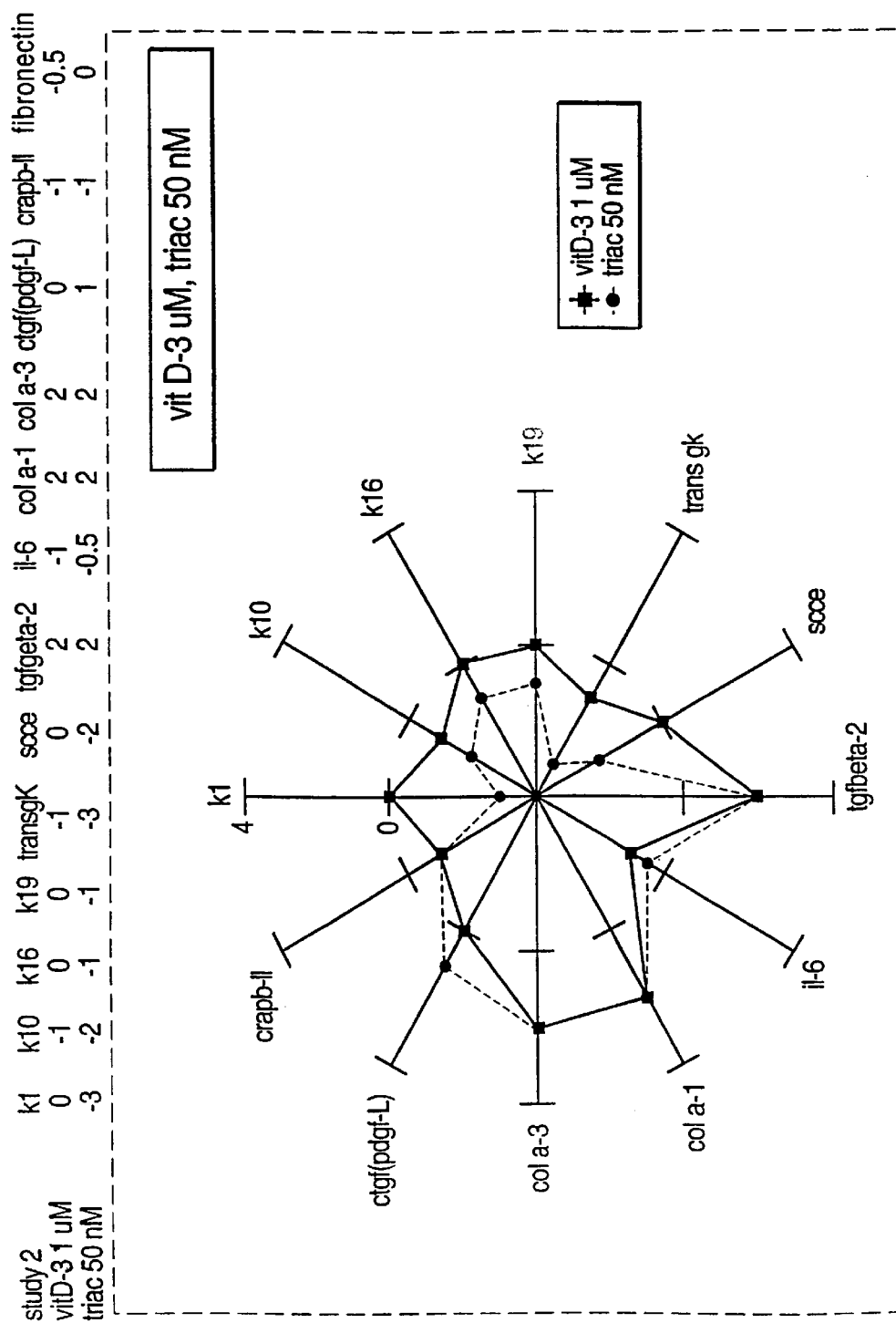
FIG. 2 is a graph showing the comparative effect of vitamin D3 and Triac on the Skin-2 model.
Figure 3:
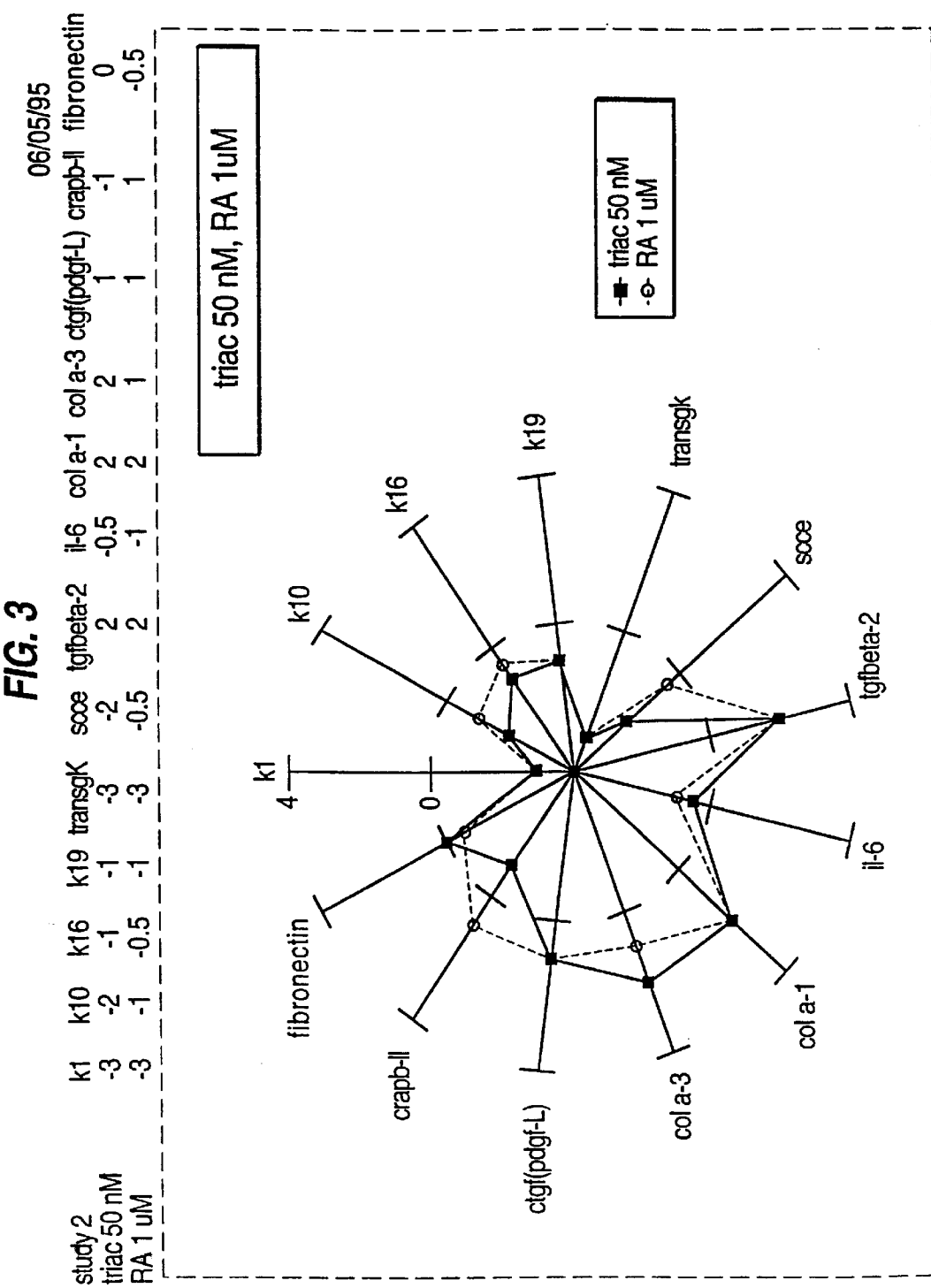
FIG. 3 is a graph showing the comparative effect of retinoic acid and Triac on the Skin-2 model.

The effect of a thyroid hormone compound, tri-iodothyroacetic acid (Triac), was first studied and compared to known medically useful compounds which affect epidermal physiology. These drugs were retinoic acid, betamethasone, and 1,25 OH vitamin D-$_3$. The semi quantitative results are shown in Table 2 and comparisons between Triac and the other drugs are displayed in FIG. 1, (betamethasone), FIG. 2 (Vit D3) and FIG. 3 (all trans Retinoic acid). Triac at 50 nMolar concentration, approximately 1000 times its affinity constant for the receptor, appears to strikingly reduce keratin 1 and 10, tranglutaminase K, and SCCE. Triac also markedly accentuates Collagen A-1 and 3A-1, along with TGF-beta-2 transcripts. In comparison with betamethasone, Triac increases collagen production and TGF beta-2 but does not strongly inhibit IL-6. The keratin findings are similar. In comparison with Triac, Vit D-3 does not inhibit the keratin gene transcripts, or SCCE or transglutaminase K, but the effect on collagen genes is similar. Retinoic acid and Triac appear very similar with the exception of only SCCE and CRAB PII. At a higher concentration, 1 $\mu$Molar, Triac continues to display the same effects although the colagen and keratin response is somewhat reduced. It is a surprising finding of the present invention that low doses of thyroid hormone compounds are dermatologically effective.

These results are consistent with known results of these drugs in other model systems. For example Vitamin D-3 is not known to affect keratinization of cultured keratinocytes. Betamethasone decreases epidermal collagen. Retinoic acid is known to decrese transglutaminase Ki and keratins 1 and 10 in culture. These results therefore suggest that Triac should have similar properties as these other medically important classes of drugs. In fact a combination of a thyroid hormone compound with a glucocorticoid should avoid the collagen loss associated with topical steroid application and add an antiinflammatory effect not seen with a thyroid hormone compound.

Figure 4:
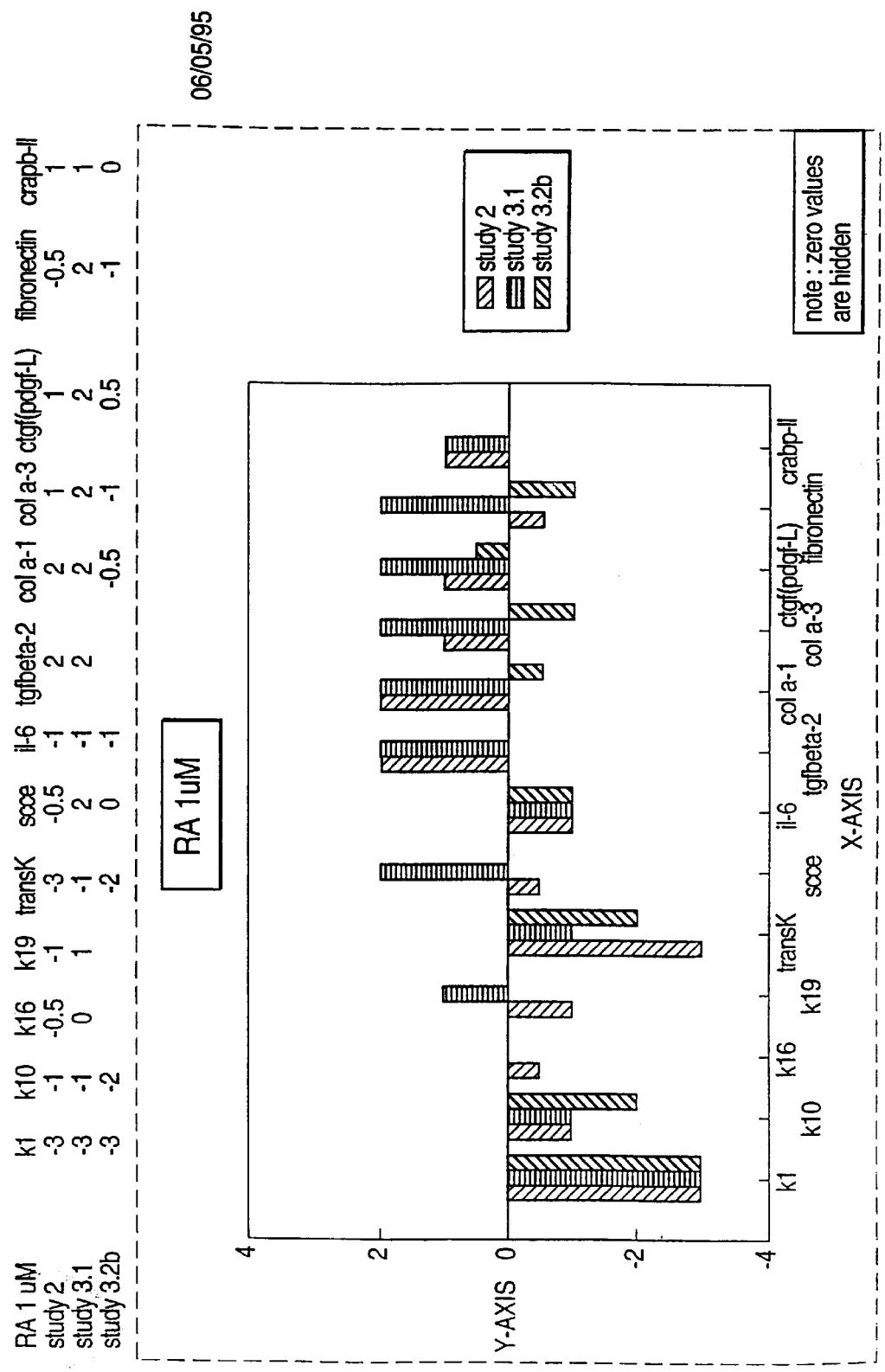
FIG. 4 is a graph showing the effect of retinoic acid on the skin-2 model in three studies.
Figure 5:
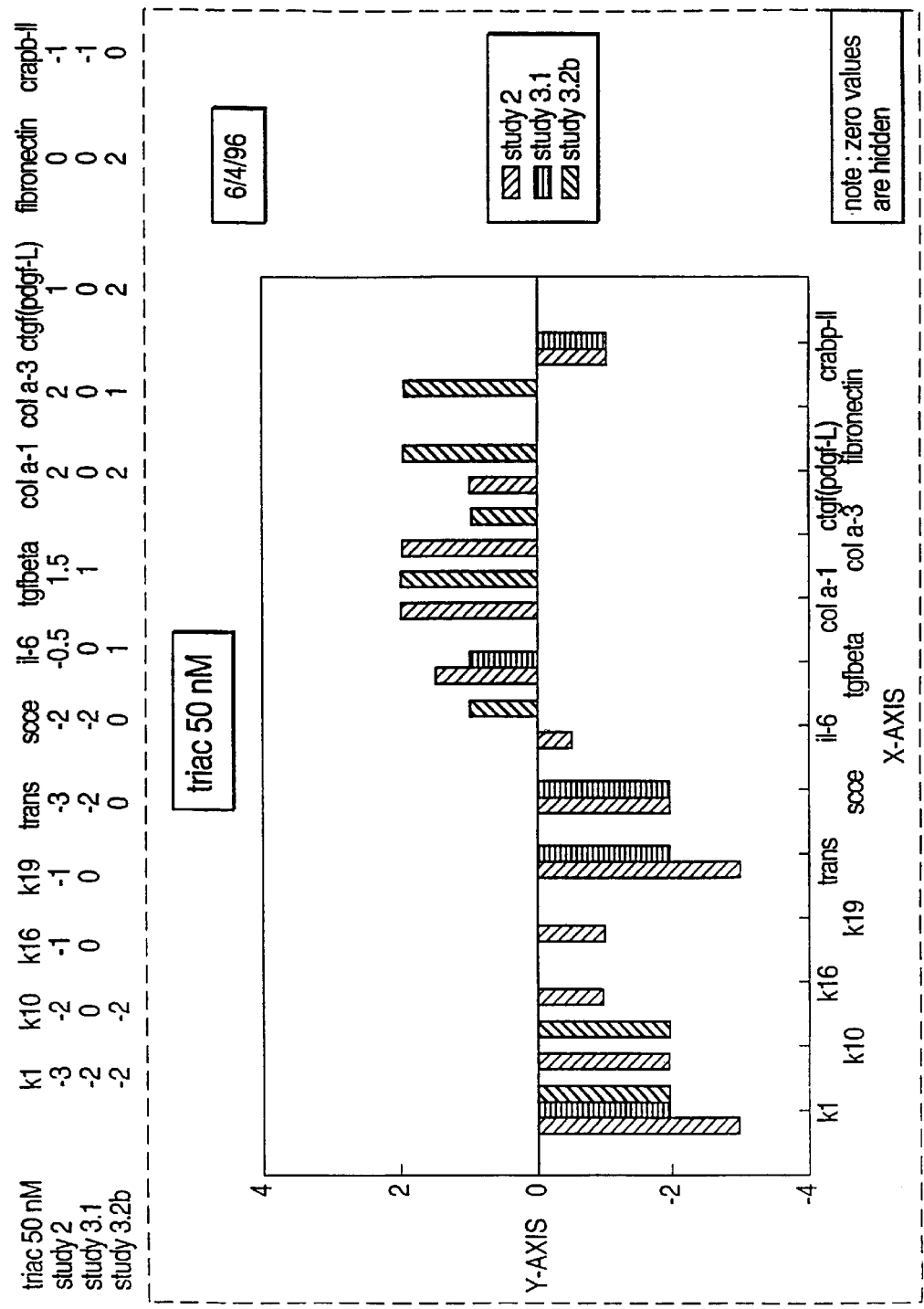
FIG. 5 is a graph showing the effect of Triac on the skin-2 model in three studies.

The results of three experiments with Triac at 50 nM dose and retinoic acid at 1 $\mu$Molar dose are shown for comparison in FIGS. 4 and 5. The two hormones appear very similar, but can be differentiated by the lack of inhibition of SCCE by RA in this model, and the modest fall in transcripts for the CRAB PII retinoid binding protein induced by Triac. Both compounds inhibit keratin 1 and more modestly, keratin 10, increase TGF-beta-2, CTGF, collagen and inhibit transglutaminase K.

A group of chemical entities were therefore tested in this model. Eight different compounds which span a range of different structures, including nonhalogenated compounds and compounds containing bromine instead of iodine, all of which bind to the receptor were assayed in the Skin-2 system. One compound, L-T-1, as described in GB7822745, GB859546 and U.S. Pat. No. 3,198,702 as part of a family of molecules which have topical utility, which bind very poorly to the receptor was also tested. The compounds were all tested at concentration ranges above their binding affinity for the receptor except for L-T-1 which binds poorly to the receptor even at the tested ten micromolar concentration. Table 3 displays the results for these compounds along with their $K_i$ (binding affinity) to the human thyroid receptor and the tested concentration of chemical. Affinities for the human thyroid receptor alpha-1 were similar. Again, a reduction in transcripts for keratin 1(8/8 compounds), keratin 10 (5/8), and transglutaminase K (4/8) was seen, along with increased collagen a-1 (7/8) and collagen 3a (6/8) and CTGF (7/8). For the most part, an inhibition of SCCE was seen, although in some instances a very modest change was displayed by some compounds. The compound (L-T-I), which did not bind to the endogenous receptor, showed no inhibition of keratin 1 or 10, a positive effect on transglutaminase K and SCCE which is opposite to the thyroid response and retinoic acid response, and only modest effects on collagen.

Certain of the compounds, notably compound number 5 displayed a relative selectively for keratin 1, tranglutaminase K and SCCE responses over collagen responses. Therefore it seems likely that some of the compounds will display a relative efficacy more weighted toward regulation of epidermal differentiation than collagen production and potential would healing effects or amelloration of dermal states characterized by collagen deficient skin.

Although the effects of these thyroid hormone compounds as a group reflect specific and reproducible changes in the transcripts of epidermally related genes which affect differentiation, the in vitro direction of the response for SCCE, Transglutaminase K and keratin 1 is the opposite to that which might be considered therapeutically useful. Since a similar result is seen for retinoic acid (Koppam et al; Griffiths et al supra), these two entities are therefore quite similar in their effects. Surprisingly the collagen response to thyroid hormone was the opposite to that reported in the literature (de Ryk et al supra). Because of the paradoxically opposite effects of retinoids on skin related proteins and genes when given in vitro as compared to in vivo testing, and the concomitant medically beneficial usefullness of retinoids. It was considered that thyroid regulation would be subject to the same paradox. therefore Triac was tested on human volunteers.

EXAMPLE 2

HUMAN STUDY THYROID HORMONE CONTROLS GENE TRANSCRIPTION IN SKIN

Three adult male volunteers ranging in age from 37–46 yrs were treated topically with a cream containing either 200 mg/100 ml or 20 mg/100 ml Triac. The cream was applied in an amount sufficient to just cover an approximately 6 cm$^2$ area on the buttocks. A similar sized area on the contralateral side, treated with a dermatologically useful cream, served as control. After application, the areas were covered with Tegaderm (3M) to prevent loss of cream and to enhance penetration. Control and Triac-treated areas were biopsied 96 h following this single treatment. The degree of erythema of each subject was judged on a subjective scale 1 to 4. Epidermis and papillary dermis from control and treated skin were obtained by manually cutting superficially with a razor-blade following 1% lidoacine anesthesia. Two pieces of tissue measuring 2×2 cm and approximately 0.2 mm in depth were obtained for RNA-preparation. The tissue was snap frozen on solid ice (–60° C.) and stored at –70° C. until used.

A large number of transcripts were tested in three male subjects and the results are shown in table 4. The change in transcription of the genes for SCCE, Keratin 1 and 10, and transglutaminase K was now unexpectedly positive, the opposite of what was found in the in vitro assay. These changes reflect an increase in the differentiation markers and suggest a change to a more terminally differentiated state. The effect on collagen and CTGF remains the same in vivo as in vitro when using the Skin-2 model. Thus, at least for gene products which are related to epidermal differentiation the thyroid response in vitro is opposite to that in vivo, an identical finding as has been seen for the medically important retinoid compounds. Moreover, the unexpected increase in collagen formation suggest utility to help rebuild photodamaged adult human skin (Talwar et al, J. Inv. Derm, 105 p285–290, 1995).

EXAMPLE 3

THYROID HORMONES ARE PHYSIOLOGICALLY ACTIVE WHEN APPLIED TO THE SKIN

Triac (Tri iodo thyroid acetic acid) or DIMIT (dimethyl isopropyl thyronine) or esters and ethers thereof are mixed in a concentration range of 10 000 000 times $K_{diss}$ to 1000 times $K_{diss}$, 100 micromolar to 1 nanomolar, in a suitable pharmacological base, such as Johnson and Johnson Purpose™ or Curity™ skin lotion and applied to hairless mice strain SKH/hr 1 for 8 weeks. Punch biopsies are obtained and ultrasound measurements were made of the skin using a 10 MHz B-mode ultrasound (18). As compared to control animals, thyroid hormone compound treated animals have an increase in the thickness of the dermal area and a slight decrease in the epidermal portion of the skin. An increased cellularity of dermal cell layers is found, with a decrease in the regularity of the rete pattern.

EXAMPLE 4

WOUND HEALING

Wounds are produced in rats and rabbits as in (19). The tensile strength of the wounds are determined at five, ten and twenty days and collagen formation in the wound determined by SDS-gel electrophoresis (20,22,23,24). Wound healing is also measured by two dimensional A and B mode ultrasound. The wounds to which thyroid hormone compound is applied have increased tensile strength and close more quickly. Ultrasound measurements disclosed a more rapid granulation base and more rapid wound closure.

EXAMPLE 5

PHOTODAMAGED SKIN

Hairless mice SKH-1 are UV-B irradiated according to the schedule of (22). After 12 weeks of irradiation, significant wrinkling results. The mice are treated with the thyroid hormone Triac-containing cream for a period of 16 weeks after irradiation. The degree of wrinkling appearing on the irradiated mice is compared to untreated, irradiated animals to which the appropriate pharmaceutical base is not applied. The thyroid hormone containing composition of the invention produces a significant decrease in the wrinkle pattern of the animals and an increase in skin collagen.

EXAMPLE 6

IMPROVEMENT IN THE APPEARANCE OF CELLULITE AND/OR REDUCTION SUBCUTANEOUS FAT DEPOSITS AND DECREASE IN SUB-CUTANEOUS DERMAL AND SUBDERMAL FAT

The thyroid compounds reverse T-3, T-3, and Triac were dissolved in 70% isopropanol-water at a concentration of 0.5 to 7 $mg/ml^{-1}$.

A hydrophillic ointment (USP) or non-USP (Fougera brand) consisting of an oil in water emulsion with suitable fatty acid modifiers in 30 ml to 100 ml amounts was placed in a suitable stirring vessel. The dissolved thyroid compounds were sprayed over the surface of the cream and mixed manually, or with a mechanical stirrer, for several minutes to produce complete mixing. To adjust for batch to batch variations in the ointment base, water or isopropanol in amounts up to 20% of the volume were added to produce a mixture which was both pleasing to touch and was easy to apply to the skin. Other solvents such as isopropanol/water, ethanol or ethanol/water were also tested for dissolution.

The cream was applied daily, twice a day or up to every three days to various parts of the body. Exercise, especially of the tested area, through dancing or mild calisthenics which produced increased warmth and blood flow to the area appeared to accelerate the effects of the cream.

EXAMPLE 6A

RIGHT BUTTOCKS

Triac, T-3 And Reverse T-3 were applied separately to the right buttock. An observer noted a decrease in the overall volume of the buttocks and a elevation of the gluteal posterior thigh fold by ½ to 1 cm. Results were noted after 10 days of application. Measurements of hip circumference showed a 0.75 inch increase in circumference after 7 days after stopping the application.

EXAMPLE 6B

RIGHT THIGH

T-3 and Triac were separately applied to a subjects right thigh for two periods of 3 weeks.
Results
The circumference of the right thigh was measured 5 cm beneath gluteal fold decreased, compared with the untreated left thigh as a control, Beginning: Right thigh measured 49 cm; Left thigh measured 47.5 cm After 20 days $T_3$ treated Right thigh measured 18.75 inches; Left thigh measured 18.5 inches.

Triac cream was then applied to Right thigh. After three weeks measurements of both thighs were the same.

There was an one pound decrease in body weight over this period.

EXAMPLE 6C

RIGHT INFRA RENAL AND SUPRA ILLIAC CREST FAT PADS

Triac cream. Test 1: applied for two weeks to right side.
Results:
Observation shows a decrease in fat pad size. Measurement of skin creases from right to left side showed: R 5.75 cm and L7.5 cm. Application stopped for two weeks and restarted with reverse T-3 cream. Effects appear similar after ten days. Photographs were taken of these areas. (See FIG. 6)

EXAMPLE 6D

RIGHT SUPRA ILLIAC CREST AND OVER ABDOMINAL RECTUS MUSCLE

Triac cream was applied to right supra illiac crest and right abdominal area.
Initial measurements: waist 28 inches, hips measured one inch below umbillicus, 36 inches After two weeks: waist 27", hips measured one inch below umbillicus 35.25 inches After 10 more days: waist 27.5" hips measured one inch below umbillicus 34 inches.

There was a body weight loss of approximately two pounds over an eight week period.

Photographs were taken of these areas as described below. Clothes fitted appreciably more easily and the appearance of diminished fat easily noted by other observers.

Figure 6:
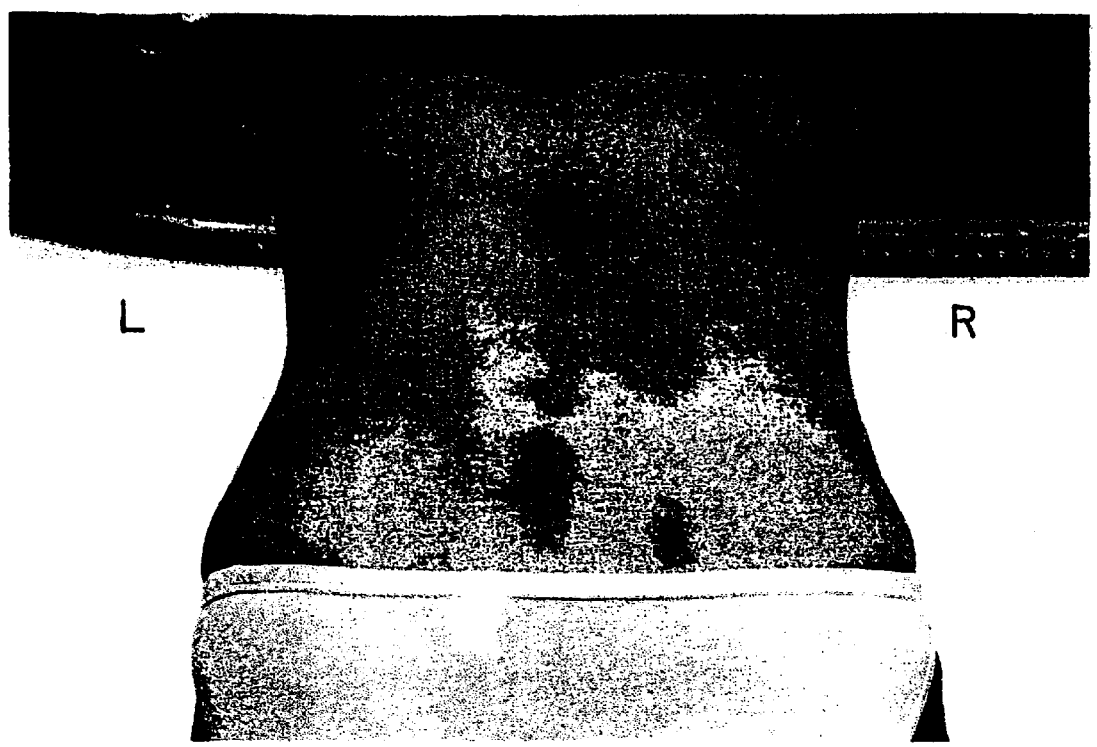
FIG. 6 is a photograph of a volunteer's waist and hip area in which a composition of the invention has been applied to the left and right side, the line drawing below emphasizing the slimming effects of the composition.
Figure 6A:
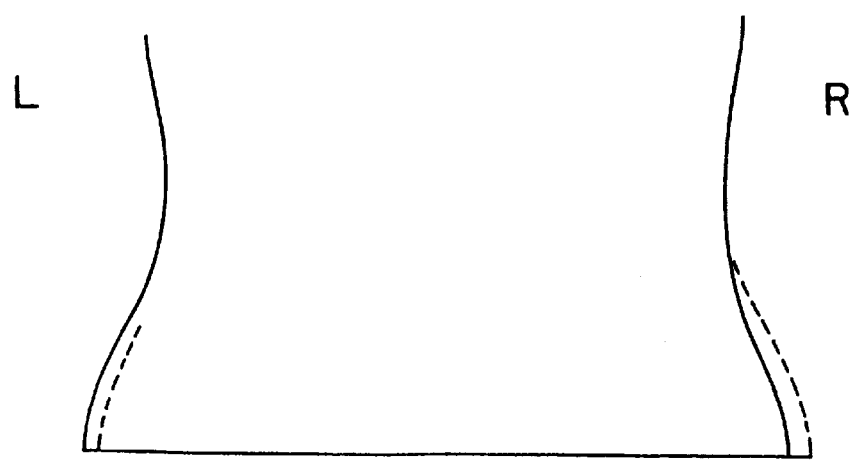
Figure 7:
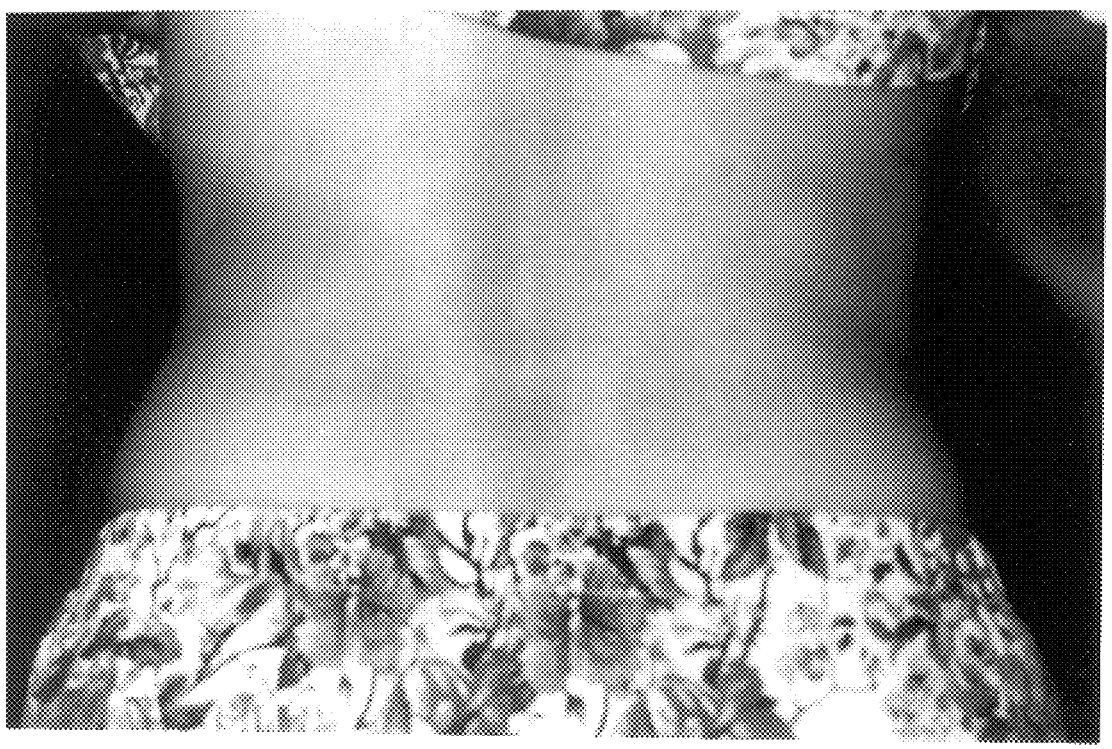
FIG. 7 is a photograph of a volunteers waist hip area in which a composition of the invention has been applied to the right side the line drawing below emphasizing the slimming effects of the composition.
Figure 7A:
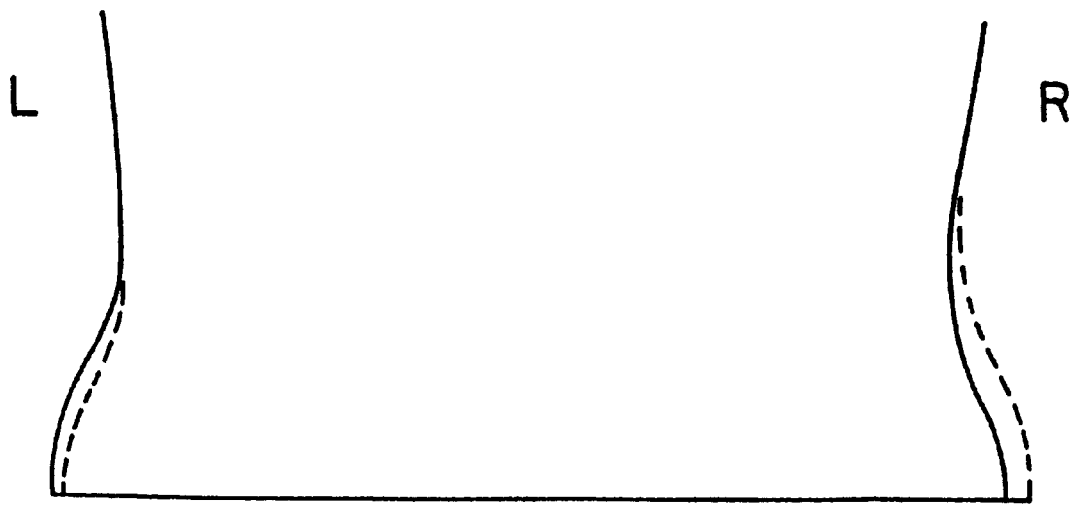

See FIGS. 6 and 7.

FIG. 6 shows the results of applying Triac and subsequently $T_3$ cream daily to the right side alone. Application of the Triac cream continued for 3.5 weeks and then was stopped for 1–2 weeks and then $T_3$ cream was applied daily for ten days. $T_3$ cream was applied daily to both sides for 7 days and then to the right side only for a further 3 days.

FIG. 7 shows the result of applying Triac cream to the right side of a volunteer on a daily basis for 3 weeks.

Figure 8:
FIG. 8 is a photograph of a volunteer's waist and hip area in which a composition of the invention has been applied to the right side the line drawing below emphasizing the slimming effects of the composition.
Figure 8A:
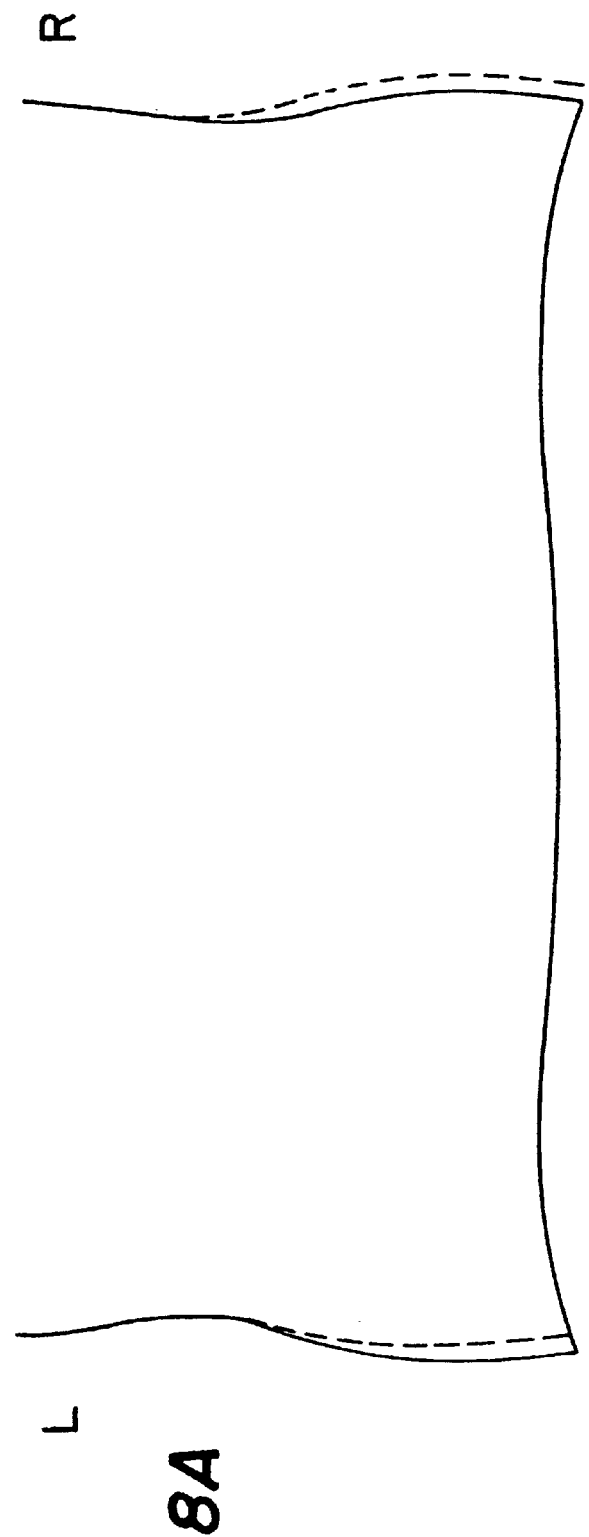

FIG. 8 shows the effect of applying $T_3$ cream to the right side of a volunteer for 3 weeks.

Thyroid gland size and radial pulse rate were measured bimonthly. No changes were observed. No hair loss, abdominal distress, cardiac arrthymia or diarrhoea were observed. No adverse changes to the underlying skin were noted.

The composition of the present invention may be conveniently supplied in a unit dose pack comprising a plastic container which may for example be bubble, or blow moulded or injected, together with a tear off plastic or foil top, the pack containing a unit dose of the composition.

EXAMPLE 7

HUMAN STUDY TREATMENT OF PSORIASIS

Patients with characterized multilateral psoriasis were subjected to a pharmacological washout period of two weeks followed by treatment of one lesion with an hydrophilic ointment containing 0.04% Triac or vehicle alone an another lesion by application of ointment twice per day. Treatment duration was 8 weeks. Clinical results were measured using a validated five point scale for the severity index of scaling, erythma and infiltration size. All observations were performed by blinded observers at two week intervals. Sixty per cent of treated patients had statistically significant and clinically significant reductions in their severity scores.

REFERENCES

1. Lavin, T. N. Mechanisms of Thyroid Hormone action. In the textbook of Endocrinology (DeGroot, Ed.), 2nd Edition, W. B. Saunders, pub. (1989).
2. Drozdzm M et al. Endokrinologie 1979 Feb; 73(1) 105–11
3. Murata Y et al J Clin Endocrinol Metab 1987 Feb; 64(2): 334–9
4. Watxke, H., et al Thrombosis Research. 46(2): 347–53, 1987 Apr 15
5. Murata Y et al JCEM 1983 Vol. 57 p. 1233–1239
6. Lee J et al Endocrinology 130 p 2733–2738, 1992
7. Ceccarelli, P et al JCEM 65 p 242–246, 1987
8. Tomio-Canic M et al Journal of Investigative Dermatology 99 p 842–847, 1992
9. Blumenberg M et al J. Invest Dermatol 1992 Jun: 98(6 Suppl): 42S–49S
10. Ohtsuki M et al J Dermatol 1992 Nov 19(11) p 774–80
11. Holt, P. J. A et al British Journal of Dermatology 95 p 513–518, 1976
12. Cronrath C M et al Endocrinology, 120(1) page 43–8, 1987 Jan
13. Towle H. C, Mariash C. N Federation Proceedings 45(9) p 2406–11, 1986 Aug.

REFERENCES -continued

14. Lemmen C. et al Biological Chemistry Hoppe–Seyler 367(7) p 533–537, 1986
15. Amorosa L. F et al Biochim Biophys Acta 1984 Feb 9, 792(2) p 192–8
16. Armer P et al Diabetes 33(4) p 369–375, 1984
17. Coronary Dru Project, JAMA 220 p 996–1008, 1972
18. Akesson, A et al Acta Radiologica Diagnosis 27 p 91–94, 12986
19. Hunt, T et al Annals Surgery 170 p 633–641, 1969
20. Varani, J et al J. Invest Dermatol 94 p 717–723, 1990
21. Loireau A et al Biochem Pharmacol 35 p 1691–1696, 1986
22. Moloney S. J et al Photochem Photobiol 56 p 505–511, 1992
23. Schwartz E et al J. Investi. Dermatol 102 p 241–246, 1994
24. Griffiths C. E. M et al NEJM 329 p 530–535, 1993
25. Roti, E et al Endocrine Reviews 14 p 401–423, 1993
26. Lev-Ran A Perspectives in Biology & Medicine 37 P 486–494, 1994
27. Apriletti J. et al J. Biol. Chem. 263 p 9409–9417, 1988

What is claimed is:

1. A skin treatment composition for topical application, the composition comprising at least one thyroid hormone compound or thyroid hormone-like compound together with a pharmacologically acceptable base, wherein said thyroid hormone compound or thyroid hormone-like compound is a chemical entity which binds to TR-α or TR-β with an equilibrium dissociation constant, $K_d$, lower than 1 μM, wherein $$K_d=(R)\cdot(L)/(RL),$$

where (R) is the concentration of receptor, (L) is the concentration of ligand, and (RL) is the concentration of the receptor-ligand complex, and wherein said skin treatment composition is effective for treating skin conditions.

2. A skin treatment composition according to claim 1, wherein said at least one thyroid hormone compound or said thyroid hormone-like compound is selected from the group consisting of Tri-iodothyronine (3,5,3'-triiodothyronine, T3); D and L thyroxine (T4); 3,3'5'tri-iodothyronine (reverse T3); 3,3'-diiodothyronine; T3 and T4 analogues such as 3,5,3',-Triiodo-L-thyronine methyl ester; 3,5,3'-Triodo-L-thyronine hydrochloride; L-thyroxine hydrochloride; Tetrac (3-[4-(4-hydroxy-3,5-diiodophenoxy)-3,5-diiodophenyl] acetic acid); Triac ([4-(4-hydroxy-3-iodophenoxy)-3,5-diiodophenyl]acetic acid); Tetraprop; Triprop ([4-(4-hydroxy-3-iodophenoxy)-3,5-diiodophenyl]propionic acid); T4Bu; T3Bu; Thyroxamine; Triiodothyronamine; (5-Benzyloxy-2-methoxyphenyl)-(2-methoxypyrimidin-5-yl)-methanol; Benzyloxy-2-methoxyphenyl)-(6-methylpyridin-3-yl)methanol; (5-Benzyloxy-2-methoxyphenyl)-(5-bromo-2-methoxypyridin-4-yl) methanol; (5-benzyloxy-2-methoxyphenyl)-(2,6-difluoropyridin-3-yl)methanol; (5-Benzyloxy-2-methoxyphenyl)-(2-methoxypyridin-4-yl)methanol; 4-Methoxy-3-[(2-methoxypyrimidin-5-yl)methyl]phenol; 4-Methoxy-3-[(6-methylpyrid-3-yl)methyl]phenol; 5-Benzyloxy-2-methoxybenzyl Bromide; (5-Benzyloxy-2-methoxyphenyl-(6-chloropyridazin-3-yl)-acetonitrile; 4-Benzyloxy-2-[2-methoxythiazol-5-yl)methyl]anisole; 6-[(5-Hydroxy-2-methoxyphenyl)methyl]thiazol-2-(3H); 3'-Heteroarylmethyl-4'-)-methyl-3,5-dinitro-N-trifluoro-acetyl-L-thyronine Ethyl Esters; 3'-heteroarylmethyl-3,5-di-iodo-4')-methyl-N-trifluoro-acetyl-L-thyronine Ethyl Esters; 3'-heteroarylmethyl analogues of 3,3',5-tri-iodo-L-thyronine (T3); 3'-substituted derivatives of the thyroid hormone 3,3'5-triiodo-L-thyronine (T3); L-3,3'-T2; DL-Br2I; L-Br2iPr; L-Me2I; L-Me3; L-Me4; L-Me2iPr;

DL-IMeI; L-3,5-Dimethyl-3'-isopropylthyronine (DIMIT); DL-BPT4; B-triac; BP-tetrac; DL-SBT3; DL-SBT4; DL-MBT3; MB-tetrac; T2F; T2Cl; T2Br; T2Me; T2Et; T2iPr; T2nPr; T2sBu; T2tBu; T2iBu; T2Phe; T2F2; T2Cl2; T2Me2; 3,5,3'-Triiodo-D-thyronine; 3,5-Diiodo-4-hydroxyphenylpropionic acid (DIHPA); Aryloxamic acids; (arylamino)acetic acids; arylpropionic acids; arylthioacetic acids; (aryloxy)acetic acid; 3,3'-T2; 3,5-T2; 3',5'-T2; α-methyl-3,5,3'-triiodothyroacetic acid, α-methyl-3,5,3'-triiodothyropropionic acid, and α-methyl-3,5,3',5'-tetraiodothyropropionic acid; methylene- and carbonyl-bridged analogs of iodinated thyronines or thyroacetic acids or iodinated benzofurans; 3,5-diiodo-4-(2-N,N-diethylaminoethoxy)phenyl-(2-butylbenzofur-3-yl) methanol hydrochloride; [2-methyl-3-(3,5-diiodo-4-(2-N,N-diethylaminoethoxy)-benzoyl)benzofuran hydrochloride;] 2-n-butyl-3-(3,5-diiodo-4-carboxymethoxy-benzoyl) benzofuran; 2-methyl-3-(3,5-diiodo-4-hydroxy-benzoyl) benzofuran; 2-methyl-3-(3,5-diiodo-4-carboxymethoxy-benzyl)benzofuran;] 4'-hydroxy-3'-iodo-3,5 diiodo-4-(2-N, N-dimethylamino-(ethoxy)benzophenone hydrochloride; 2-butyl-3-(3-iodo-4-hydroxybenzoyl)benzfuran; 4',4-dihydroxy 3'3,5-triiodo-diphenylmethane; [3,5-diiodo-4-(2-N,N-diethylaminoethoxy)phenyl-(2-butylbenzofur-3-yl) methanol hydrochloride; 2-methyl-3-(3,5-diiodo-4-(2-N,N-diethylaminoethoxy)-benzoyl)benzofuran hydrochloride; 2-n-butyl-3-(3,5-diiodo-4-carboxymethoxy-benzoyl) benzofuran; 2-methyl-3-(3,5-diiodo-4-hydroxy-benzoyl) benzofuran; 2-methyl-3-(3,5-diiodo-4-carboxymethoxy-benzyl)benzofuran; 4'-hydroxy-3'-iodo-3,5-diiodo-4-(2-N, N-dimethylamino-ethoxy)benzophenone hydrochloride; 2-butyl-3-(3-iodo-4-hydroxybenzoyl)benzofuran; 4',4-dihydroxy-3'3,5-triiodo-diphenylmethane;] 3,5-diethyl,3'-isopropyl thyronine (DIET); and IpTA2 (3,5 diiodo-3'isopropyl thyroacetic acid) and pharmacologically acceptable salts and derivatives thereof.

3. A composition according to claim 1 comprising a concentration of $5 \times 10^8$ times $K_d$ or less of the said at least one thyroid hormone compound or said thyroid hormone-like compound.

4. A composition according to claim 1 in which the said at least one thyroid hormone compound or said thyroid hormone-like compound is in chemically pure form.

5. A composition according to claim 1 in which the pharmacologically acceptable base is selected from oil in water emulsions, sprays, liposomes and solutions.

6. A composition according to claim 1, in which the said at least one thyroid hormone compound or said thyroid hormone-like compound is at least partially dissolved in a solvent.

7. A composition according to claim 6 in which the solvent is an organic solvent.

8. A composition according to claim 7 in which the organic solvent is selected from alcohol and alcohol and water solutions.

9. A composition according to claim 8 in which the organic solvent is selected from isopropanol, isopropanol and water, ethanol, and ethanol and water solutions.

10. A composition according to claim 1, wherein said skin condition is selected from the group consisting of stria, cellulite, roughened skin, actinic skin damage, intrinsically aged skin, photodamaged skin, lichen planus, ichthyosis, acne, psoriasis, wrinkled skin, Dernier's disease, eczema, atopic dermatitis, seborrhoeic dermatitis scleroderma, collagen deficient skin, glucocorticoid induced atrophy, chloracne, pityriasis, and skin scarring.

11. A composition according to claim 1, further comprising at least one compound selected from the group consisting of a Vitamin D analogue, a glucocorticoid and a retinoid acid receptor binding compound.

12. A unit dose package containing a single dose of a composition according to claim 1.

13. A method of improving the skin condition of a subject, the method comprising the steps of: providing a composition in accordance with claim 1; and applying the said composition to the skin of the subject.

14. The method according to claim 13, in which said skin condition is selected from the group consisting of stria, cellulite, roughened skin, actinic skin damage, intrinsically aged skin, photodamaged skin, lichen planus, ichthyosis, acne, psoriasis, wrinkled skin, Dernier's disease, eczema, atopic dermatitis, seborrhoeic dermatitis scleroderma, collagen deficient skin, glucocorticoid induced atrophy, chloracne, pityriasis, and skin scarring.

15. A method according to claim 13 in which the composition is applied from twice a day to every three days.

16. A composition according to claim 1, comprising less than or equal to about 50 mg/100 ml of thyroid hormone compound or thyroid hormone-like compound.

17. A composition according to claim 16 comprising less than or equal to about 20 mg/100 ml of thyroid hormone compound or thyroid hormone-like compound.

18. The skin treatment composition of claim 1, wherein said composition affects an improvement in the skin's condition without resulting in systemic metabolism of the compound.

19. The skin treatment composition of claim 1, wherein a medically or cosmetically sufficient amount of thyroid hormone compound or thyroid hormone-like compound enters the skin but in which substantially no thyroid hormone compound or thyroid hormone-like compound subsequently has a serum concentration which is physiologically adverse after topical application of the compound.

20. The skin treatment composition of claim 1, further comprising an additional ingredient selected from the group consisting of medicinal herbs, butylated hydroxytoluene, butylated hydroxyanisole, para-aminobenzoic acid, Tinuvin P, and combinations thereof.

21. The skin treatment composition of claim 20, wherein said medicinal herbs are selected from the group consisting of Guto Kola, Cola nitada, Khella, cola nut, Camellia Suiensis, Guavana, clove, coffee, and combinations thereof.

22. A method of modulating the expression of genes in the skin, the method comprising applying a composition comprising at least one thyroid hormone compound or said thyroid hormone-like compound together with a pharmacologically acceptable base to the skin, wherein said thyroid hormone compound or said thyroid hormone-like compound is a chemical entity which binds to TR-α or TR-β with a dissociation constant, $K_d$, lower than 1 μM.

23. A method according to claim 16 in which the gene to modulated is selected from genes encoding keratin 1, keratin 10, TGF beta-2, TGF-alpha, TGF beta-1, SCCE, Transglutaminase K, Keratin growth factor (KGF), procollagen 1A1, procollagen 3A-1, keratin 16, connective tissue growth factor CTGF, CRABP-II.

24. A method of reducing subcutaneous fat deposits in a subject, the method comprising the steps of applying a composition to skin of the subject, said composition comprising at least one thyroid hormone compound or thyroid hormone-like compound together with a pharmacologically acceptable base, wherein said thyroid hormone compound or thyroid hormone-like compound is a chemical entity which binds to TR-α or TR-β with an equilibrium dissociation constant, $K_d$, lower than 1 μM, wherein $$K_d=(R)\cdot(L)/(RL),$$

where (R) is the concentration of receptor, (L) is the concentration of ligand, and (RL) is the concentration of the receptor-ligand complex, and wherein said subcutaneous fat deposits are reduced.

25. A method according to claim 24 in which the composition is applied to the skin from between twice a day to every three days.

* * * * *